US012649795B2

(12) United States Patent
Guo et al.

(10) Patent No.: US 12,649,795 B2
(45) Date of Patent: Jun. 9, 2026

(54) ANTI-INSULIN-LIKE GROWTH FACTOR 1 RECEPTOR (IGF-1R) ANTIBODIES AND METHOD OF USE THEREOF TO TREAT THYROID-ASSOCIATED OPTHAMOLOGY

(71) Applicant: Suzhou Pro-heal Pharmaceuticals technology Co., Ltd., Jiangsu (CN)

(72) Inventors: Shuhua Guo, Jiangsu (CN); Lin Ma, Jiangsu (CN); Peng Zhang, Jiangsu (CN)

(73) Assignee: Suzhou Pro-heal Pharmaceuticals technology Co., Ltd., Jiangsu (CN)

( * ) Notice: Subject to any disclaimer, the term of this patent is extended or adjusted under 35 U.S.C. 154(b) by 834 days.

(21) Appl. No.: 17/938,674

(22) Filed: Oct. 7, 2022

(65) Prior Publication Data

US 2023/0127946 A1     Apr. 27, 2023

Related U.S. Application Data

(63) Continuation-in-part of application No. PCT/CN2021/077939, filed on Feb. 25, 2021.

(30) Foreign Application Priority Data

Apr. 10, 2020     (CN) .......................... 202010280882.7

(51) Int. Cl.
| | |
|---|---|
| *C07K 16/28* | (2006.01) |
| *A61K 39/00* | (2006.01) |
| *A61P 27/02* | (2006.01) |

(52) U.S. Cl.
CPC .......... *C07K 16/2863* (2013.01); *A61P 27/02* (2018.01); *A61K 2039/505* (2013.01); *C07K 2317/33* (2013.01); *C07K 2317/92* (2013.01)

(58) Field of Classification Search
CPC ........... C07K 16/2863; C07K 2317/33; C07K 2317/56; C07K 2317/92; A61P 27/02; A61P 5/16; A61K 2039/505; A61K 2039/55; C12N 15/85
See application file for complete search history.

(56) References Cited

U.S. PATENT DOCUMENTS

| | | | | |
|---|---|---|---|---|
| 7,871,611 | B2 * | 1/2011 | Calzone | .................. A61P 25/00 |
| | | | | 530/387.3 |
| 8,476,409 | B2 * | 7/2013 | Baum | .................... C07K 16/30 |
| | | | | 530/387.5 |
| 2006/0018910 | A1 | 1/2006 | Gualberto et al. | |
| 2009/0175868 | A1 | 7/2009 | Ludwig et al. | |
| 2010/0158919 | A1 | 6/2010 | Dauphin et al. | |
| 2014/0193404 | A1 | 7/2014 | Hansen et al. | |
| 2019/0040141 | A1 | 2/2019 | Beltran et al. | |

FOREIGN PATENT DOCUMENTS

| | | |
|---|---|---|
| CN | 101415728 | 4/2009 |
| CN | 101657469 | 2/2010 |
| CN | 101842117 | 9/2010 |
| CN | 102123712 | 7/2011 |
| CN | 102164960 | 8/2011 |
| CN | 102725000 | 10/2012 |
| CN | 109803679 | 5/2019 |
| WO | 2004087756 | 10/2004 |
| WO | 2019136405 | 7/2019 |

OTHER PUBLICATIONS

Martinez P, et al. (2014) Expert Opinion on Investigational Drugs. 23(10):1423-1432. (https://doi.org/10.1517/13543784.2014.951434).*
"International Search Report (Form PCT/ISA/210) of PCT/CN2021/077939," mailed on May 28, 2021, with English translation thereof, pp. 1-10.

* cited by examiner

*Primary Examiner* — Robert S Landsman
(74) *Attorney, Agent, or Firm* — COOPER LEGAL GROUP LLC

(57)     ABSTRACT

The invention provides an antibody that can bind IGF-1R. The antibody is composed of light chain and heavy chain. The light chain and heavy chain variable regions are one of the combinations of SEQ ID NO:2 and SEQ ID NO:3, SEQ ID NO:4 and SEQ ID NO:5, SEQ ID NO:6 and SEQ ID NO:7, SEQ ID NO:8 and SEQ ID NO:9, SEQ ID NO:10 and SEQ ID NO:11, SEQ ID NO:12 and SEQ ID No 13, SEQ ID NO:14 and SEQ ID NO:15. The invention also provides nucleic acid molecules encoding the antibody binding IGF-1R, vectors containing the nucleic acid, cells transformed by the vectors, and uses of these nucleic acids, vectors, and cells.

4 Claims, 2 Drawing Sheets

Specification includes a Sequence Listing.

1

ANTI-INSULIN-LIKE GROWTH FACTOR 1 RECEPTOR (IGF-1R) ANTIBODIES AND METHOD OF USE THEREOF TO TREAT THYROID-ASSOCIATED OPTHAMOLOGY

CROSS-REFERENCE TO RELATED APPLICATION

The present application is a continuation-in-part of PCT application No. PCT/CN2021/077939, filed on Feb. 25, 2021, which claims the priority of China Patent Application No. 202010280882.7, filed on Apr. 10, 2020, and now issued as China Patent 113512116B. The entirety of each of the above mentioned patent applications is incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Oct. 4, 2022, is named 125997 SEQUENC-ING-LIST and is 22,453 bytes in size.

BACKGROUND

Technical Field

The present invention relates to the field of biomedicine. More specially, the invention concerns anti-IGF-1R antibodies and uses thereof.

Description of Related Art

Thyroid associated ophthalmopathy (TAO), sometimes known as endocrine exophthalmos, infiltrative exophthalmos or thyroid ophthalmopathy, shares about 20% of orbital related diseases. TAO may cause proptosis, eyelid contracture, extraocular muscle dysfunction, bulbar conjunctival congestion, periorbital edema, etc, and seriously lead to exposure keratitis, diplopia and compressive optic neuropathy of which the latter could result in blindness and greatly affects the quality of life of patients. TAO is a tissue-specific autoimmune disease triggered by common antigen expressed from thyroid epithelial cells, anterior orbital adipocytes and fibroblast, and mainly rely on cellular immunity. Exophthalmos resulted from inflammatory reaction, increase of orbital fibroblasts and orbital adipocytes is a kind of symptom of TAO. Insulin-like growth factor 1 receptor (IGF-1R) and Thyroid-stimulating hormone receptor (TSHR) present abnormally high expression level in orbital fibroblasts in patients with TAO, and there is a complex signal pathway cross-talking between the IGF-1R and TSHR, which shows that it is closely related to the occurrence of disease.

IGF-1R belongs to the tyrosine protein kinase receptor family. It is a transmembrane protein on the cell surface, which can be activated by IGF-1 and IGF-2 (both insulin growth factors). Its overexpression may be related to multiple sclerosis, Crohn's disease, pulmonary fibrosis and other malignant tumors and autoimmune diseases. anti-IGF-1R antibodies can be detected in most patients with TAO, but few in normal people. IgG isolated from the serum of patients with TAO can replace IGF-1R and bind to the site on the surface of orbital fibroblasts. IGF-1R or TAO associated IgG can activate IGF-1R positive orbital fibroblasts from patients with TAO. Thus, akt/frap/mtor/p70s6k pathways are activated to induce the expression of interleukin-16 and RANTES (regulated on activation in normal T-Cell expressed and secreted) on orbital fibroblasts, promote the synthesis of T cell chemokines, and cause the inflammatory infiltration of T lymphocytes and the production of hyaluronic acid, all of which indicate that IGF-1R may be involved in the development of TAO as a secondary antigen. In addition, it has been reported that IGF-1R and TSHR have a large amount of downstream signal overlap, and the monoclonal antibody against IGF-1R can block the signal transduction of IGF-1R, weaken the downstream signal of TSHR pathway, and reduce the inflammatory response caused by thyrotropin, suggesting that IGF-1R is involved in TSHR signal transduction, and IGF-1R and TSHR may form a functional complex, which plays a synergistic role in the abnormal signal transduction related to TAO disease.

Anti-anti-IGF-1R antibody (see patents WO2004087756, US20100158919, US20140193404) has reached the primary and all secondary end points in clinical trials for the treatment of TAO, with significantly improving the symptoms of proptosis. In addition to the antibodies listed above, there are no other anti-IGF-1R antibodies at home and abroad for the treatment of TAO except that some are used to treat cancer such as anti-IGF-1R antibodies mentioned in parent CN200880011970.4, CN200880114015.3, CN200780011979.0, CN200980137723.3, US20190040141, US20090175868, US20060018910. It's necessary to develop new anti-IGF-1R therapeutic antibodies for the treatment of TAO.

SUMMARY

In order to solve the above problems, the present invention provides an antibody against IGF-1R and its application in drugs. The antibody and related drugs can be used for the prevention or treatment of TAO.

In an aspect, the disclosure features an antibody that binds to IGF-1R.

The antibody is composed of light chain and heavy chain.

The light chain variable region (VL) of the antibody is any one of SEQ ID NO:2, SEQ ID NO:4, SEQ ID NO:6, SEQ ID NO:8, SEQ ID NO:10, SEQ ID NO:12, SEQ ID NO:14.

In some embodiments, the invention provides an antibody whose light chain constant region (CL) is SEQ ID NO:16.

In some embodiments, the invention provides an antibody whose light chain includes the light chain variable region and the light chain constant region shown in SEQ ID no:16.

The heavy chain variable region (VH) of the antibody is any one of SEQ ID NO:3, SEQ ID NO:5, SEQ ID NO:7, SEQ ID NO:9, SEQ ID NO:11, SEQ ID NO:13, SEQ ID NO:15.

In some embodiments, the invention provides an antibody whose heavy chain constant region (CH) is SEQ ID NO:17.

In some embodiments, the invention provides an antibody whose heavy chain of includes the heavy chain variable region and the heavy chain constant region shown in SEQ ID NO:17.

In some embodiments, the invention provides an antibody including SEQ ID NO:2 and SEQ ID NO:3 as VL and VH.

In some embodiments, the invention provides an antibody including SEQ ID NO:4 and SEQ ID NO:5 as VL and VH.

In some embodiments, the invention provides an antibody including SEQ ID NO:6 and SEQ ID NO:7 as VL and VH.

In some embodiments, the invention provides an antibody including SEQ ID NO:8 and SEQ ID NO:9 as VL and VH.

In some embodiments, the invention provides an antibody including SEQ ID NO:10 and SEQ ID NO:11 as VL and VH.

In some embodiments, the invention provides an antibody including SEQ ID NO:12 and SEQ ID NO:13 as VL and VH.

In some embodiments, the invention provides an antibody including SEQ ID NO:14 and SEQ ID NO:15 as VL and VH.

The disclosure also features through an interchain disulfide bond.

In various embodiments of the above-described antibodies thereof, the light chain and the heavy chain of the antibody are connected by an interchain disulfide bond.

In another aspect, the disclosure features a nucleic acid molecule encoding the antibody obtained by any of the above technical schemes.

In another aspect, the disclosure features a vector including the nucleic acid molecule which encode the antibody obtained by any of the above technical schemes.

In another aspect, the disclosure features a cell including the aforementioned vector.

In another aspect, the disclosure features the uses of the above-described antibodies for preparation of medicine for TAO.

In some embodiments, the uses are preparing medicine for TAO by the above-described antibodies, the nucleic acid molecule encoding the above-described antibodies, the vector including the nucleic acid molecule which encode the above-described antibodies, the cell including the aforementioned vector.

In some embodiments, the antibody is separated and purified.

In some embodiments, the nucleic acid molecule encoding the above-described antibodies, the vector including the nucleic acid molecule which encode the above-described antibodies, or the cell including the aforementioned vector expresses the above-described antibodies to use.

In some embodiments, the above-described antibodies, the nucleic acid molecule encoding the above-described antibodies, the vector including the nucleic acid molecule which encode the above-described antibodies, or the cell including the aforementioned vector is added to the medicine to use.

In some embodiments, the use is for TAO including but not limited to: proptosis, eyelid retraction, delayed upper eyelid descent, extraocular muscle hypertrophy, conjunctival congestion, periorbital tissue edema, eyelid insufficiency, photophobia, tears, foreign body sensation, vision loss or diplopia.

In another aspect, the disclosure features a method of preparing the above-described anti-IGF-1R antibodies.

The method is using the nucleotide sequence encode the anti-IGF-1R antibody to construct an expression vector and transfect a cell, thus the anti-IGF-1R antibody is obtained through the expression of the product in the cell.

In another aspect, the disclosure features a pharmaceutical composition.

The pharmaceutical composition includes one or more of the anti-IGF-1R antibodies, the nucleic acid molecule encoding the above-described antibodies, the vector including the nucleic acid molecule which encode the above-described antibodies, or the cell including the aforementioned vector is added to the medicine to use.

In some embodiments, there is one or both of pharmaceutically acceptable carriers and excipients in the pharmaceutical composition.

In some embodiments, the pharmaceutically acceptable carriers and excipients include but are not limited to: solubilizer and stabilizer and excipients.

In some embodiments, the administration methods of the pharmaceutical composition include but are not limited to subcutaneous injection, intradermal injection, intramuscular injection, intravenous injection, intravenous drip and eyelid injection.

In some embodiments, the pharmaceutical composition is applied to the prevention and/or treatment of TAO, which including but not limited to eyeball protrusion, eyelid retraction, upper eyelid tardive, extraocular muscle hypertrophy, conjunctival congestion, periorbital tissue edema, eyelid insufficiency, photophobia, tears, foreign body sensation, vision loss or diplopia.

DESCRIPTION OF THE EMBODIMENTS

Figure 1:
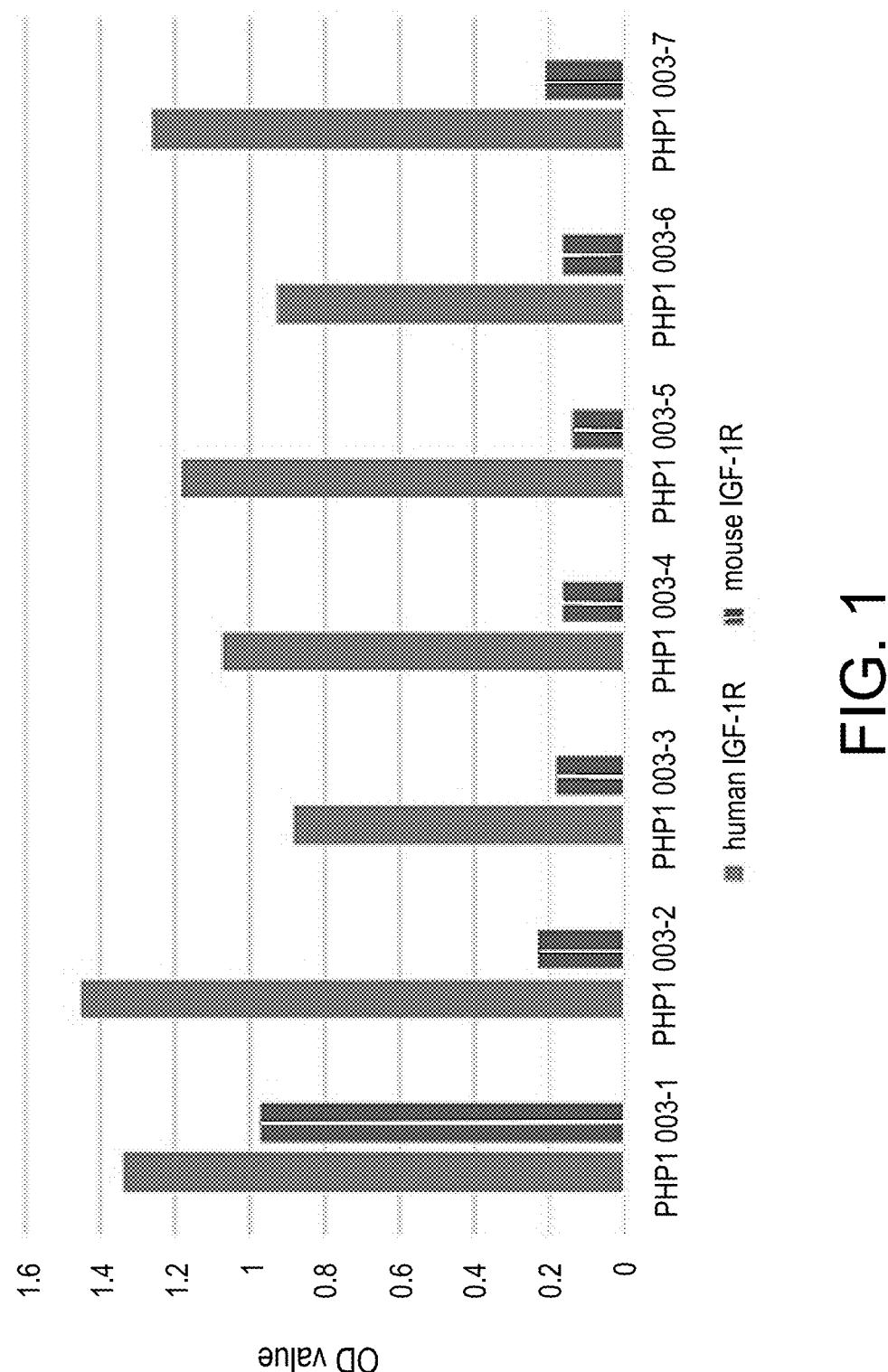
FIG. 1 shows the ELISA results of anti-IGF-1R antibodies binding to human IGF-1R protein and mouse IGF-1R protein.

The invention is described in further detail below in combination with specific embodiments. The following embodiments are not used to limit the invention, but only to illustrate the invention. If there is no special description for the experimental method used in the following examples, and the experimental method without specific conditions specified in the examples, usually according to the conventional conditions, the materials and reagents used in the following examples, if there is no special description, can be obtained from commercial channels.

Example 1 Sequence Synthesis and Vector Construction of Anti-IGF-1R Antibody Light chain design: the light chain variable region and the light chain constant region are directly spliced to form a light chain.

Heavy chain design: the heavy chain variable region and the heavy chain constant region are directly spliced to form a light chain.

For the amino acid sequence of light chain and heavy chain, the codon was optimized according to the human host cell and the gene was synthesized routinely. At the same time, 5 '(EcoRI digestion site) and 5'UTR (seq ID NO:20) and 3'UTR (tgatga) and 3' (HindIII digestion site) were added.

The above genes were synthesized by Suzhou GENEWIZ Biotechnology Co., Ltd.

The gene was cloned into vector pTT5 (ampicillin resistance) through 5'EcoRI and 3'HindIII. Select clones for sequencing, select the bacteria with correct sequencing for seed preservation and expand the culture of the bacteria. The expanded bacteria are used for plasmid extraction. The combination of light chain recombinant vector and heavy chain recombinant vector was respectively named PHP1003-1, PHP1003-2, PHP1003-3, PHP1003-4, PHP1003-5, PHP1003-6 and PHP1003-7. According to the same gene synthesis and vector construction method as above, the plasmid expressing the control antibody was obtained, in which the light chain sequence of the positive control antibody was such as SEQ ID NO:18 and the heavy chain sequence was such as SEQ ID NO:19.

The sequence of the light and heavy chain in this embodiment is as table 1:

TABLE 1

Light and heavy chains of anti-IGF-1R antibodies

| | Sequence composition |
|---|---|
| PHP1003-1 light chain | VL: SEQ ID NO: 2, CL: SEQ ID NO: 16 |
| PHP1003-1 heavy chain | VH: SEQ ID NO: 3, CH: SEQ ID NO: 17 |
| PHP1003-2 light chain | VL: SEQ ID NO: 4, CL: SEQ ID NO: 16 |
| PHP1003-2 heavy chain | VH: SEQ ID NO: 5, CH: SEQ ID NO: 17 |
| PHP1003-3 light chain | VL: SEQ ID NO: 6, CL: SEQ ID NO: 16 |
| PHP1003-3 heavy chain | VH: SEQ ID NO: 7, CH: SEQ ID NO: 17 |
| PHP1003-4 light chain | VL: SEQ ID NO: 8, CL: SEQ ID NO: 16 |
| PHP1003-4 heavy chain | VH: SEQ ID NO: 9, CH: SEQ ID NO: 17 |
| PHP1003-5 light chain | VL: SEQ ID NO: 10, CL: SEQ ID NO: 16 |
| PHP1003-5 heavy chain | VH: SEQ ID NO: 11, CH: SEQ ID NO: 17 |
| PHP1003-6 light chain | VL: SEQ ID NO: 12, CL: SEQ ID NO: 16 |
| PHP1003-6 heavy chain | VH: SEQ ID NO: 13, CH: SEQ ID NO: 17 |
| PHP1003-7 light chain | VL: SEQ ID NO: 14, CL: SEQ ID NO: 16 |
| PHP1003-7 heavy chain | VH: SEQ ID NO: 15, CH: SEQ ID NO: 17 |
| Control antibody | Light chain: SEQ ID NO: 18, heavy chain: SEQ ID NO: 19 |

Example 2 Transient Expression of Anti-IGF-1R Antibodies and Detection of Binding IGF-1R Protein The extracted plasmid was transfected and antibodies were separated and purified in the following way:

1. Measure the cell density, and the viability should be greater than 95%. Adjust the HEK293 cell density to 3 with (preheated) HEK293 medium×10$^6$ cells/mL, gently shake well and repack the cells (the transfection amount is 90% of the transfection system). Note that the cell volume in the shaking flask does not exceed ⅓ of the specification of the shaking flask, and put it into the shaking table for use.

2. Calculate the volume of transfection buffer opti-MEM according to the volume of transfected cells, which is ⅒ of the transfection system; Calculate the amount of transfection reagent PEI, and the proportion is 3 μL/mL transfected cells; Calculate the total amount of transfected DNA, and the proportion is 1 μg/mL transfected cells.

The specific operation process of transfection is as follows:

Take a 50 ml centrifuge tube, add 10% MEM of the transfection system, add plasmids, mix well, filter, stand for 5 min, add PEI to the DNA suspension, gently mix well (gently reverse the mixing for 2-3 times), and then stand for 15-20 min. Then gently add the complex into the sub packed cells, and gently shake the flask while adding; The transfected cells were cultured in a 37° C. shaking table.

After 14 days of culture, the culture supernatant was collected by centrifugation, and purify the antibodies with affinity purification column. Octet RED96 protein interaction workstation was used to detect the affinity of the above purified antibodies with human IGF-1R (Human IGF-1R, ARCO, No. IGR-H5229) separately. Biosensor AHC (18-5060) was used to capture the samples, and then the captured samples were compared with human IGF-1R. The dynamics of binding and dissociation of monkey IGF-1R and rat IGF-1R proteins were detected. Dynamics uses 1:1 combined model for fitting analysis. The brief action steps are: protein loading for 200 s, binding for 180 s, dissociation for 300 s, regeneration for 30 s.

Affinity was determined using Fortebio instruments. The results are shown in table 2:

TABLE 2

Ability of anti-IGF-1R antibodies to bind IGF-1R protein

| Anti-IGF-1R antibody | Antigen | Affinity (M) | Binding constant (1/Ms) | Dissociation constant (1/s) | Fitting R^2 |
|---|---|---|---|---|---|
| PHP1003-1 | Human | 1.27E−09 | 2.74E+05 | 3.47E−04 | 0.9913 |
| PHP1003-2 | IGF-1R | 3.83E−09 | 2.28E+05 | 8.74E−04 | 0.9983 |
| PHP1003-3 | protein | 1.85E−09 | 4.07E+05 | 7.54E−04 | 0.9826 |
| PHP1003-4 | | 5.91E−09 | 2.47E+05 | 1.46E−03 | 0.9907 |
| PHP1003-5 | | 7.01E−10 | 5.65E+05 | 3.96E−04 | 0.9334 |
| PHP1003-6 | | 1.12E−09 | 4.22E+05 | 4.72E−04 | 0.9859 |
| PHP1003-7 | | 8.98E−09 | 9.83E+04 | 8.83E−04 | 0.9952 |

Example 3 Cross Reactivity of Anti-IGF-1R Antibodies

The antigen binding ability to human IGF-1R protein and mouse IGF-1R protein (Acro, IGR-R5224) of the antibodies purified in Example 2 was determined with ELISA method. Briefly, human IGF-1R protein and mouse IGF-1R protein with a concentration of 1 μg/mL were coated respectively overnight, after which add purified antibody (1 μg/mL) for incubation, and then detect absorbance after combined with anti-human IgG HRP (Thermofish, 31410). The results are shown in FIG. 1.

It can be seen from the results of ELISA that only antibody PHP1003-1 can bind both human IGF-1R protein and mouse IGF-1R protein at the same time.

Example 4 Biological Activity of Anti-IGF-1R Antibodies

IGF-1R signaling pathway plays an important role in the proliferation, differentiation and metastasis of tumor cells. The activation of IGF-1R can promote the proliferation of some cells, such as MCF7 cells, while inhibition of IGF-1R activity can inhibit cell proliferation. Therefore, the activity of anti-IGF-1R antibodies in our invention can be evaluated by detecting the cell proliferation of MCF-7.

CCK8 method was used to detect the inhibitory efficiency of anti-IGF-1R antibody on MCF7 cell proliferation. The steps were as follows:

1. Day 1: MCF-7 cells were seeded with a density of 5×10$^3$ cells/hole;
2. Day 2: After overnight culture, MCF-7 cells were incubated for 96 hours with anti-IGF-1R antibodies in different concentration gradients;
3. Day 3: Detected OD450 after incubation with CCK8 solution (10 μL/hole) for 4 h.

The proliferation of MCF-7 cells was determined by adding purified chimeric antibodies (anti-IGF-R antibodies) of different concentrations. The inhibitory results of different antibodies on the proliferation of MCF-7 cells are shown in table3:

TABLE 3

Inhibitory results of anti-IGF-R antibodies on the proliferation of MCF-7 cells

| Antibody | IC50 (μg/mL) |
|---|---|
| PHP1003-1 | 2.37 |
| PHP1003-2 | 3.93 |
| PHP1003-3 | 1.16 |
| PHP1003-4 | 4.05 |

TABLE 3-continued

| Inhibitory results of anti-IGF-R antibodies on the proliferation of MCF-7 cells | |
| --- | --- |
| Antibody | IC50 (µg/mL) |
| PHP1003-5 | 0.96 |
| PHP1003-6 | 3.81 |
| PHP1003-7 | 2.14 |

Example 5 Efficacy of Anti-IGF-1R Antibody PHP1003-1 and Positive Control Antibody in Hyperthyroidism Animal Model In this Example, the hyperthyroidism and TAO model of rats was induced by intraperitoneal injection of bovine thyroglobulin, and the effect of PHP1003-1 on TAO of rats was observed, including the following steps:

(1) The rats in the model group were injected with bovine thyroglobulin (SigmaAldrich, 609310) intraperitoneally at the dose of 150 µg/piece every two weeks, which lasted for 4 weeks.

(2) The test objects and the control object were administered respectively. The grouping of experimental animals is shown in table 4:

TABLE 4

| Grouping of experimental animals | | | |
| --- | --- | --- | --- |
| Group | Treatment | Objects | Concentration |
| Sham Group | Normal saline injection | — | — |
| Vehicle Group | Bovine thyroglobulin injection | PBS | — |
| L. Group | | PHP1003-1 | 1 mg/kg |
| H. Group | | PHP1003-1 | 2.5 mg/kg |
| P. Group | | Positive control antibody | 2.5 mg/kg |

There are 5 groups as follows: normal control group (Sham Group), negative control group (Vehicle Group), testing antibody treatment group (PHP1003-1-L. Group; PHP1003-1-H. Group), positive control antibody group (P. Group).

The administration plan is listed in the following table 5:

TABLE 5

| Administration of experimental animals | | | | | |
| --- | --- | --- | --- | --- | --- |
| Group | Treatment | Objects | Route | Concentration | Frequency |
| Sham Group | Normal saline injection | — | — | — | Once/w, 4 w in total |
| Vehicle Group | Bovine thyroglobulin injection | PBS | i.m | — | |
| PHP1003-1-L. Group | | PHP1003-1 | | 1 mg/kg | |
| PHP1003-1-H. Group | | PHP1003-1 | | 2.5 mg/kg | |
| P. Group | | Control antibody | | 2.5 mg/kg | |

(3) Animals were euthanized 4 weeks after administration. After euthanasia, the extraocular muscles of rats were taken for tissue staining and observing under optical microscope.

Figure 2:
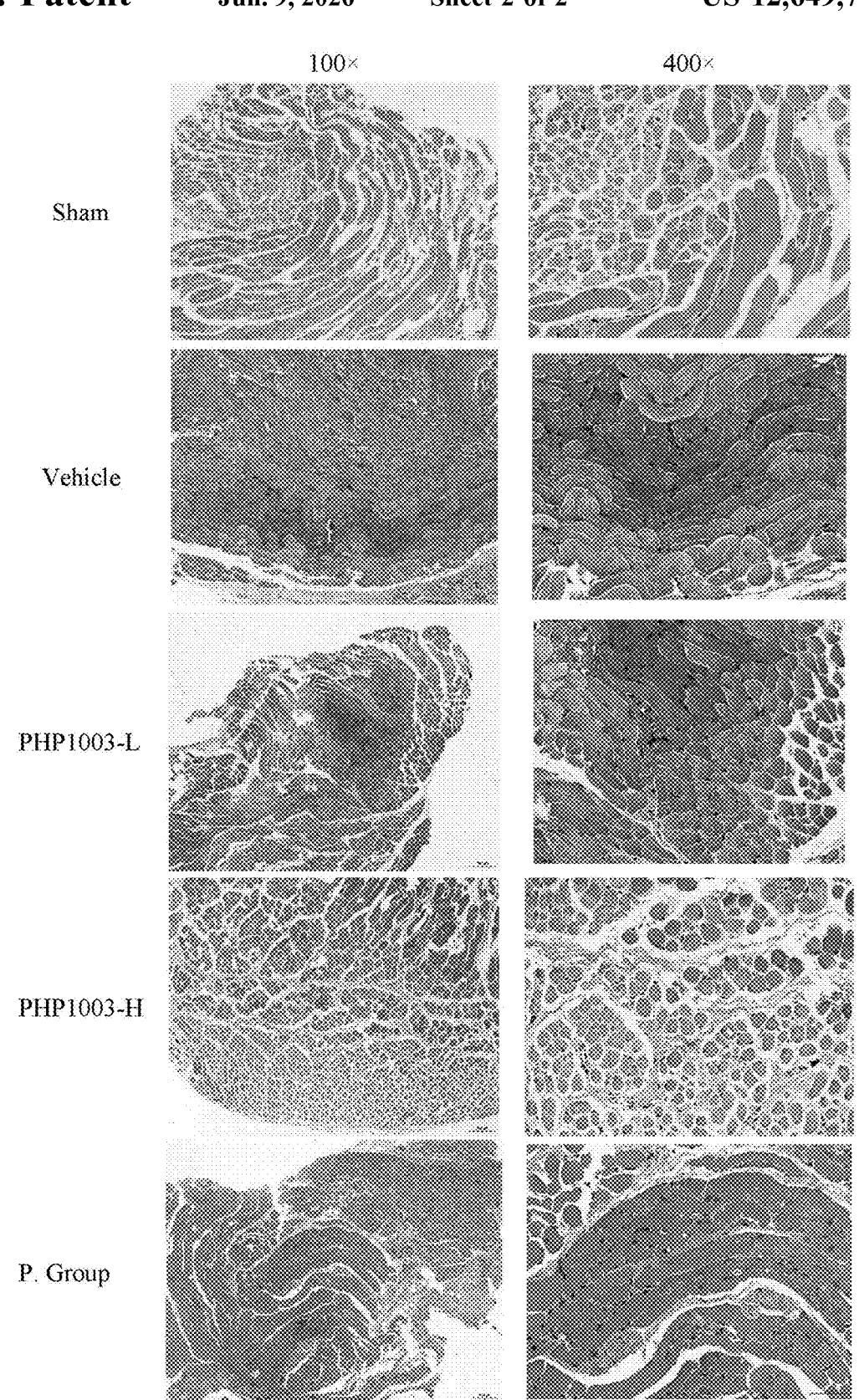
FIG. 2 shows the IHC results of extraocular muscles of rats with different treatment methods.

(4) The results are shown in FIG. 2:

In Sham Group, muscle fibers were homogeneous and red stained, arranged neatly, with abundant intramuscular capillaries and normal muscle spacing. Various extraocular muscle lesions were seen in Vehicle Group, mainly including severe swelling, degeneration, necrosis and dissolution of muscle fibers, narrowing or widening of muscle spacing, and proliferation of fibrotic tissue and blood vessels between muscles. It is suggested that the TAO model of SD rats has been successfully generated.

The visible lesions in PHP1003-1-L. Group basically cover all kinds of lesions in Vehicle Group, and the degree of muscle fiber necrosis and degeneration is slightly less than that in Vehicle Group. PHP1003-1-H. Group has slight pathological changes, and the muscle fibers are basically arranged neatly, and some muscle fibers are slightly swollen or denatured, indicating that PHP1003-1-H. Group has a certain effect on TAO in SD rats. The staining results of extraocular muscles in P. Group showed that the swelling, hypertrophy, muscle fiber degeneration and necrosis of extraocular muscles were less severe than those in Vehicle Group. The results showed that both PHP1003-1-H. Group and P. Group could reduce the pathological degree of extraocular muscles in rats with TAO. Compared with P. Group, the pathological degree of extraocular muscles in SD rats in PHP1003-1-H. Group was milder, and the swelling degree of extraocular muscles in P. Group was greater, and the muscle spacing was narrower, indicating that PHP1003-1-H. Group had better therapeutic effect on TAO in SD rats than P. group at the same dose.

What is claimed is:

1. An anti-IGF-1R antibody, comprising any one of SEQ ID NO: 2, SEQ ID NO:4, SEQ ID NO:6, SEQ ID NO:8, SEQ ID NO:10, SEQ ID NO: 12, SEQ ID NO:14 as a light chain variable region (VL); and any one of SEQ ID NO: 3, SEQ ID NO:5, SEQ ID NO:7, SEQ ID NO:9, SEQ ID NO: 11, SEQ ID NO: 13, SEQ ID NO:15 as a heavy chain variable region (VH), wherein the VL and VH's combination is one of SEQ ID NO:2 and SEQ ID NO:3, SEQ ID NO:4 and SEQ ID NO: 5, SEQ ID NO:6 and SEQ ID NO:7, SEQ ID NO:8 and SEQ ID NO:9, SEQ ID NO: 10 and SEQ ID NO:11, SEQ ID NO: 12 and SEQ ID NO:13, SEQ ID NO:14 and SEQ ID NO:15, wherein the light chain comprises VL and light chain constant region (CL) as SEQ ID NO:16; and the heavy chain comprises VH and heavy chain constant region (CH) as SEQ ID NO:17.

2. A pharmaceutical composition, comprising the antibody of claim 1.

3. A method for treatment or adjuvant treatment of thyroid-associated ophthalmopathy (TAO), comprising:

administering the antibody of claim 1 as a drugs.

4. The method of claim 3, wherein the TAO comprises exophthalmos, eyelid retraction, delayed upper eyelid descent, extraocular muscle hypertrophy, conjunctival congestion, periorbital tissue edema, eyelid insufficiency, photophobia, tears, foreign body sensation, decreased vision or diplopia.

* * * * *

SEQUENCE LISTING

```
Sequence total quantity: 20
SEQ ID NO: 1           moltype = AA  length = 1337
FEATURE                Location/Qualifiers
source                 1..1337
                       mol_type = protein
                       organism = synthetic construct
SEQUENCE: 1
EICGPGIDIR NDYQQLKRLE NCTVIEGYLH ILLISKAEDY RSYRFPKLTV ITEYLLLFRV   60
AGLESLGDLF PNLTVIRGWK LFYNYALVIF EMTNLKDIGL YNLRNITRGA IRIEKNADLC  120
YLSTVDWSLI LDAVSNNYIV GNKPPKECGD LCPGTMEEKP MCEKTTINNE YNYRCWTTNR  180
CQKMCPSTCG KRACTENNEC CHPECLGSCS APDNDTACVA CRHYYYAGVC VPACPPNTYR  240
FEGWRCVDRD FCANILSAES SDSEGFVIHD GECMQECPSG FIRNGSQSMY CIPCEGPCPK  300
VCEEEKKTKT IDSVTSAQML QGCTIFKGNL LINIRRGNNI ASELENFMGL IEVVTGYVKI  360
RHSHALVSLS FLKNLRLILG EEQLEGNYSF YVLDNQNLQQ LWDWDHRNLT IKAGKMYFAF  420
NPKLCVSEIY RMEEVTGTKG RQSKGDINTR NNGERASCES DVLHFTSTTT SKNRIIITWH  480
RYRPPDYRDL ISFTVYYKEA PFKNVTEYDG QDACGSNSWN MVDVDLPPNK DVEPGILLHG  540
LKPWTQYAVY VKAVTLTMVE NDHIRGAKSE ILYIRTNASV PSIPLDVLSA SNSSSQLIVK  600
```

-continued

```
WNPPSLPNGN LSYYIVRWQR QPQDGYLYRH NYCSKDKIPI RKYADGTIDI EEVTENPKTE    660
VCGGEKGPCC ACPKTEAEKQ AEKEEAEYRK VFENFLHNSI FVPRPERKRR DVMQVANTTM    720
SSRSRNTTAA DTYNITDPEE LETEYPFFES RVDNKERTVI SNLRPFTLYR IDIHSCNHEA    780
EKLGCSASNF VFARTMPAEG ADDIPGPVTW EPRPENSIFL KWPEPENPNG LILMYEIKYG    840
SQVEDQRECV SRQEYRKYGG AKLNRLNPGN YTARIQATSL SGNGSWTDPV FFYVQAKTGY    900
ENFIHLIIAL PVAVLLIVGG LVIMLYVFHR KRNNSRLGNG VLYASVNPEY FSAADVYVPD    960
EWEVAREKIT MSRELGQGSF GMVYEGVAKG VVKDEPETRV AIKTVNEAAS MRERIEFLNE   1020
ASVMKEFNCH HVVRLLGVVS QGQPTLVIME LMTRGDLKSY LRSLRPEMEN NPVLAPPSLS   1080
KMIQMAGEIA DGMAYLNANK FVHRDLAARN CMVAEDFTVK IGDFGMTRDI YETDYYRKGG   1140
KGLLPVRWMS PESLKDGVFT TYSDVWSFGV VLWEIATLAE QPYQGLSNEQ VLRFVMEGGL   1200
LDKPDNCPDM LFELMRMCWQ YNPKMRPSFL EIISSIKEEM EPGFREVSFY YSEENKLPEP   1260
EELDLEPENM ESVPLDPSAS SSSLPLPDRH SGHKAENGPG PGVLVLRASF DERQPYAHMN   1320
GGRKNERALP LPQSSTC                                                  1337

SEQ ID NO: 2           moltype = AA   length = 112
FEATURE                Location/Qualifiers
source                 1..112
                       mol_type = protein
                       organism = synthetic construct
SEQUENCE: 2
DVVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQGTHWP LTFGQGTKVE IK           112

SEQ ID NO: 3           moltype = AA   length = 119
FEATURE                Location/Qualifiers
source                 1..119
                       mol_type = protein
                       organism = synthetic construct
SEQUENCE: 3
QVQLQESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYCARWT GRTDAFDIWG QGTMVTVSS    119

SEQ ID NO: 4           moltype = AA   length = 107
FEATURE                Location/Qualifiers
source                 1..107
                       mol_type = protein
                       organism = synthetic construct
SEQUENCE: 4
EIVLTQSPGT LSVSPGERAT LSCRASQSIG SSLHWYQQKP GQAPRLLIKY ASQSLSGIPD    60
RFSGSGSGTD FTLTISRLEP EDFAVYYCHQ SSRLPHTFGQ GTKVEIK                 107

SEQ ID NO: 5           moltype = AA   length = 118
FEATURE                Location/Qualifiers
source                 1..118
                       mol_type = protein
                       organism = synthetic construct
SEQUENCE: 5
EVQLVQSGGG LVKPGGSLRL SCAASGFTFS SFAMHWVRQA PGKGLEWISV IDTRGATYYA    60
DSVKGRFTIS RDNAKNSLYL QMNSLRAEDT AVYYCARLGN FYYGMDVWGQ GTTVTVSS     118

SEQ ID NO: 6           moltype = AA   length = 112
FEATURE                Location/Qualifiers
source                 1..112
                       mol_type = protein
                       organism = synthetic construct
SEQUENCE: 6
DIVMTQSPLS LPVTPGQPAS ISCRSSQSIV HSNGNTWLQW WLQKPGQSPQ LLIWKVSNRL    60
WGVPDRFSGS GSGTDFTLKI SRVQAQDVGV WWCFQGSHVP WTFGQGTKVQ IK           112

SEQ ID NO: 7           moltype = AA   length = 117
FEATURE                Location/Qualifiers
source                 1..117
                       mol_type = protein
                       organism = synthetic construct
SEQUENCE: 7
QVQLQQSGPG LVKPSQTLSL TCTVSGWSIS GGWLWNWIRQ PPGKGLQWIG WISWDGTNNW    60
KPSLKDRVTI SVDTSKNQFS LKLSSVTAAD TAVWWCARWG RVFFDWWGQG TLVTVSS      117

SEQ ID NO: 8           moltype = AA   length = 108
FEATURE                Location/Qualifiers
source                 1..108
                       mol_type = protein
                       organism = synthetic construct
SEQUENCE: 8
SSELTQDPAV SVALGQTVRI TCQGDSLRSY YATWYQQKPG QAPILVIYGE NKRPSGIPDR    60
FSGSSSGNTA SLTITGAQAE DEADYYCKSR DGSGQHLVFG GGTKLTVL                108

SEQ ID NO: 9           moltype = AA   length = 130
FEATURE                Location/Qualifiers
```

-continued

```
source                  1..130
                        mol_type = protein
                        organism = synthetic construct
SEQUENCE: 9
EVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCARAP LRFLEWSTQD HYYYYYMDVW  120
GKGTTVTVSS                                                         130

SEQ ID NO: 10           moltype = AA   length = 107
FEATURE                 Location/Qualifiers
source                  1..107
                        mol_type = protein
                        organism = synthetic construct
SEQUENCE: 10
DIQMTQFPSS LSASVGDRVT ITCRASQGIR NDLGWYQQKP GKAPKRLIYA ASRLHRGVPS   60
RFSGSGSGTE FTLTISSLQP EDFATYYCLQ HNSYPCSFGQ GTKLEIK                107

SEQ ID NO: 11           moltype = AA   length = 125
FEATURE                 Location/Qualifiers
source                  1..125
                        mol_type = protein
                        organism = synthetic construct
SEQUENCE: 11
EVQLLESGGG LVQPGGSLRL SCTASGFTFS SYAMNWVRQA PGKGLEWVSA ISGSGGTTFY   60
ADSVKGRFTI SRDNSRTTLY LQMNSLRAED TAVYYCAKDL GWSDSYYYYY GMDVWGQGTT  120
VTVSS                                                              125

SEQ ID NO: 12           moltype = AA   length = 108
FEATURE                 Location/Qualifiers
source                  1..108
                        mol_type = protein
                        organism = synthetic construct
SEQUENCE: 12
DIQLTQSPSS LSASVGDRVT ITCKASQEVG TAVAWYQQKP GKAPKLLIYW ASTRHTGVPS   60
RFSGSGSGTD FTFTISSLQP EDIATYFCQQ YSNYPLTFGQ GTKVEIKR               108

SEQ ID NO: 13           moltype = AA   length = 121
FEATURE                 Location/Qualifiers
source                  1..121
                        mol_type = protein
                        organism = synthetic construct
SEQUENCE: 13
QVQLQESGGG VVQPGRSLRL SCSASGFTFS DYYMYWVRQA PGKGLEWVAY ITNYGGSTYY   60
PDTVKGRFTI SRDNAKNTLF LQMDSLRPED TGVYFCARQS NYDYDGWFAY WGQGTPVTVS  120
S                                                                  121

SEQ ID NO: 14           moltype = AA   length = 112
FEATURE                 Location/Qualifiers
source                  1..112
                        mol_type = protein
                        organism = synthetic construct
SEQUENCE: 14
DIVMTQSPLS LPVTPGEPAS ISCRSSQSIV HSNGNTYLQW YLQKPGQSPQ LLIYKVSNRL   60
YGVPDRFSGS GSGTDFTLKI SRVEAEDVGV YYCFQGSHVP WTFGQGTKVE IK          112

SEQ ID NO: 15           moltype = AA   length = 117
FEATURE                 Location/Qualifiers
source                  1..117
                        mol_type = protein
                        organism = synthetic construct
SEQUENCE: 15
QVQLQESGPG LVKPSETLSL TCTVSGYSIT GGYLWNWIRQ PPGKGLEWIG YISYDGTNNY   60
KPSLKDRVTI SRDTSKNQFS LKLSSVTAAD TAVYYCARYG RVFFDYWGQG TLVTVSS     117

SEQ ID NO: 16           moltype = AA   length = 107
FEATURE                 Location/Qualifiers
source                  1..107
                        mol_type = protein
                        organism = synthetic construct
SEQUENCE: 16
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 17           moltype = AA   length = 330
FEATURE                 Location/Qualifiers
source                  1..330
                        mol_type = protein
                        organism = synthetic construct
SEQUENCE: 17
```

-continued

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 18            moltype = AA  length = 215
FEATURE                  Location/Qualifiers
source                   1..215
                         mol_type = protein
                         organism = synthetic construct
SEQUENCE: 18
EIVLTQSPAT LSLSPGERAT LSCRASQSVS SYLAWYQQKP GQAPRLLIYD ASKRATGIPA   60
RFSGSGSGTD FTLTISSLEP EDFAVYYCQQ RSKWPPWTFG QGTKVESKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 19            moltype = AA  length = 448
FEATURE                  Location/Qualifiers
source                   1..448
                         mol_type = protein
                         organism = synthetic construct
SEQUENCE: 19
QVELVESGGG VVQPGRSQRL SCAASGFTFS SYGMHWVRQA PGKGLEWVAI IWFDGSSTYY   60
ADSVRGRFTI SRDNSKNTLY LQMNSLRAED TAVYFCAREL GRRYFDLWGR GTLVSVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 20            moltype = DNA  length = 66
FEATURE                  Location/Qualifiers
source                   1..66
                         mol_type = other DNA
                         organism = synthetic construct
SEQUENCE: 20
gccaccatgg agacagatac cctgctgctg tgggtgctgc tgctgtgggt ccctggcagc   60
accgga                                                             66
```